United States Patent [19]

Wright et al.

[11] Patent Number: 4,881,562
[45] Date of Patent: Nov. 21, 1989

[54] HEART VALVE AND XENOGRAFT WASHING SYSTEM

[75] Inventors: Diana R. Wright, Conifer, Colo.; David W. Schlerf, Martinez, Calif.

[73] Assignee: Pioneering Technologies, Inc., Wheat Ridge, Colo.

[21] Appl. No.: 345,180

[22] Filed: May 1, 1989

Related U.S. Application Data

[62] Division of Ser. No. 167,707, Mar. 14, 1988, Pat. No. 4,838,288.

[51] Int. Cl.[4] .......................... B08B 3/04; B08B 11/02
[52] U.S. Cl. ..................................... 134/110; 134/201; 206/523
[58] Field of Search .................... 134/95, 99, 102, 103, 134/110, 111, 113, 182, 186, 188, 191, 195, 201; 422/29, 292; 206/523

[56] References Cited

U.S. PATENT DOCUMENTS

| | | | |
|---|---|---|---|
| 3,543,776 | 12/1970 | Layton | 134/110 |
| 3,904,058 | 9/1975 | Rosenstein | 260/523 X |
| 4,054,220 | 10/1977 | Rosenstein | 206/523 X |
| 4,056,921 | 11/1977 | Gilliand et al. | 134/102 X |
| 4,064,886 | 12/1977 | Heckele | 134/102 X |
| 4,101,031 | 7/1978 | Cromie | 206/523 X |
| 4,216,860 | 8/1980 | Heimann | 206/523 X |
| 4,731,154 | 3/1988 | Hazlitt et al. | 134/113 X |
| 4,738,272 | 4/1988 | McConnell | 134/95 X |

Primary Examiner—Philip R. Coe
Attorney, Agent, or Firm—Grant L. Hubbard

[57] ABSTRACT

A packaged prosthesis and a system and method for washing prosthetic and other implants with a biologically compatible wash solution prior to implantation, which allows for complete washing of valve and graft tissue to remove preservatives used to store the tissue grafts and or treat the same, having containers containing the wash solution, a sterile filter in fluid communication with these containers, a valve to the sterile filter to control the flow of wash solution from the containers to the sterile filter and a wash chamber, in fluid communication with the sterile filter, for positioning the prosthesis or tissue implant to permit wash solution to flow freely over and wash the same are disclosed.

4 Claims, 3 Drawing Sheets

HEART VALVE AND XENOGRAFT WASHING SYSTEM

This is a divisional of co-pending application of Ser. No. 167,707 filed on Mar. 14, 1988 and now U.S. Pat. No. 4,838,288.

FIELD OF THE INVENTION

This invention relates to apparatus and processes for washing prosthetic and other implants which require extended or repeated washing to remove preservatives or liquid reagent treatment, or both.

BACKGROUND OF THE INVENTION

Xenogeneic tissue, implant tissue from species different than the implanted species, is useful for replacing human organs damaged by pathological or physical injury. Xenografts are used for replacing heart valves, tendons, skin, blood vessels, ligaments, etc.

Xenografts are treated by several processes for cross-linking the predominate collagen to render the xenografts less susceptible to degradative mechanisms of the human system. Xenografts are preserved in sterile solutions, usually a dilute solution of glutaraldehyde or formaldehyde following treatment, during shippment and awaiting implantation. While the apparatus and methods of this invention are not so limited, the washing of heart valve prostheses will be described to illustrate and exemplify the invention. A typical tissue heart valve prosthesis is made of a porcine heart or of membrane tissue mounted on a stent. The tissue is treated with various reagents to cross-link the collogen, alter the characteristics of the tissue, etc. and is preserved in a glutaraldehyde or formaldehyde or other solution which contains a preservative and/or bacteriostatic compound. For descriptive purposes, glutaraldehyde solutions will be discussed as exemplary, though the particular nature of the solution is not critical to the invention. It is extremely important that all of the glutaraldehyde, formaldehyde or other preservative solutions be removed from the valve before it is implanted in the patient. Some chemical treatments create the risk that some toxic response will be encountered in sensitive individuals, even after general washing of the xenograft prior to implantation. Frolova, M. A.; Barbarash, L. S.; Gudkova, R. G. Carpinskaya, B. M., *The Effect of Various Preservation Methods on Immunoqenicity and Antiqenic Composition of Xenoqeneic Valve Tissue of the Heart*, Byull. Eksp. Biol. Med., Volume No. 3, 1973, pp. 83–86.

The washing step has been tedious, time consuming and must be accomplished immediately before surgery. The general methods of rinsing the xenograft prior to implantation have not substantially decreased the risk of toxic response by completely removing the preservative. The present invention is designed to provide a system for complete washing of valve and graft tissues with a maximum of efficiency and a minimum of inconvenience and time.

SUMMARY OF THE INVENTION

The invention is a system for washing heart valve prosthesis, xenografts and other implants which require extended or repeated washing to remove a preservative and/or to pre-treat the prosthesis immediately before implantation.

The system typically includes a number of disposable containers of saline solution, or other wash solution. Sterile polyethylene or other polymeric containers are readily available and are conveniently used in this invention. Flow of wash solution from the containers controlled by a valve or a series of valves through a sterile filter and then through the wash chamber containing the prosthesis thoroughly washes the prosthesis many times and removes all soluble constituents of the preservative medium. The effluent from the wash chamber passes through a reaction chamber, controlled by suitable valves, which comprises a detection device for determining the presence or absence of preservatives in the effluent wash solution, thus permitting the operator to be certain that the xenograft has been thoroughly washed and that all preservative has been removed. The detection device may include any of several chemical and instrumental analytical systems and apparatus, such as, for example, a photometer, membrane electrode, polarimeter, oxidation-reduction cell, or indicator solution. The specific method for detecting the absence or presence of the preservatives is not critical. For example, an indicator for aldehydes may be metered into a reaction chamber, providing a color change based on the presence of aldehydes. Another sterile filter may be provided in the effluent line as the effluent wash solution is drained to a suitable waste disposable system. These filters assure the continued sterility of the system. The sterile filters can be checked to assure that no bacteria or other organisms have entered into the system.

The flow in the wash chamber is preferrably directed to flow over all of the surfaces of the heart valve or graft which is to be washed. The heart valve or other tissue prosthesis can be washed with very little attention, and with a high degree of confidence that the washing is complete.

The wash chamber is preferrably designed as a shipping and storage package functioning to preserve as well as wash the heart valve prosthesis. In a preferred form the wash chamber comprises a funnel with specific prosthesis supports designed to support the particular prosthesis in a configuration which will permit the fluid to wash all surfaces and a cap having means configured to direct the flow of the wash solution over the prosthesis. In a preferred form, a filter cloth surrounds the prosthesis and breaks down any jets of wash solution and difuses the flow over the surfaces of the prosthesis. The cap and funnel are constructed and configred to provide a relatively high velocity, low instantaneous volume fluid flow around the valve and through the sewing ring.

The invention is, in its preferred configuration, an integral package functioning as a storage and wash chamber, which may include a built-in recirculating pump to increase the efficiency of the washing and/or treating of the prosthesis. The heart valve prosthesis is placed within the chamber, which is filled with a suitable preservative solution Seals close the top and bottom conduits of the chamber, which are configured to be connected to tubing, valves, etc. to complete the system. The chamber thus formed by the funnel and cap is enclosed in a heat sealable polyethylene or other polymeric material pouch to provide physical protection, and to serve as a tamper indicator and dust/lint protector and to maintain sterility. The pouch is then, typically, placed in an expanded polystyrene shell for shock protection and to moderate temperature extremes during shipping.

The prosthesis is prepared for implantation by removing the cap seals, draining the storage solution, and connecting the wash chamber to tubes to which are connected to allow the flow of saline solution through the chamber and over the prosthesis. In the preferred embodiment, a built-in recirculationg pump, fully prepared to run and supplied with batteries, may be turned on immediately without further preparation. The heart valve prosthesis is maintained in its proper washing configuration in the wash chamber to prevent damage before implantation. The prosthesis is then ready to be implanted without risk of a toxic reaction due to the presence of preservatives. The wash solution may perform the additional function of coating or treating the prosthesis with any desired reagent immediately before the prosthesis is implanted. Some or all of the wash solution may contain the treating reagent. For example, the final wash phases of the process may very desirably include the step of flowing a solution carrying epithelial cells for coating the prosthesis with the epithelial cells immediately before the prosthesis is implanted in the patient.

DESCRIPTION OF THE PREFERRED EMBODIMENT

The invention is described using as an example a porcine heart valve prosthesis, with the understanding that any prosthetic device which requires washing before use is contemplated within the scope of the invention.

Figure 1:
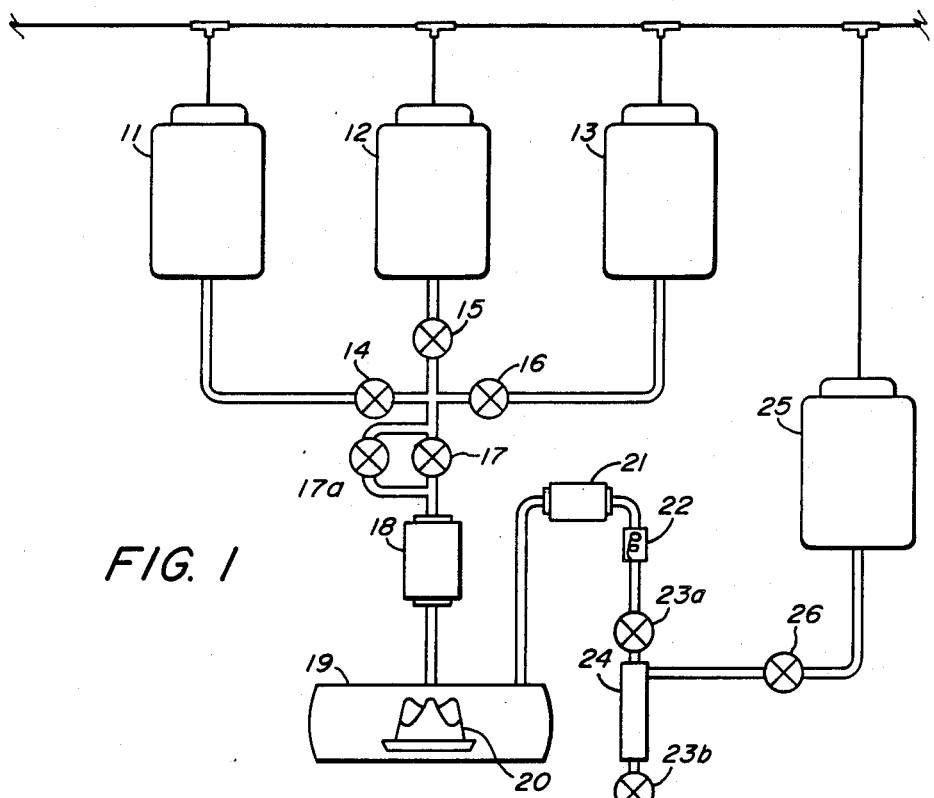
FIG. 1 is a schematic diagram of the xenograft washing system of this invention.

Referring to FIG. 1, the system of the invention comprises one or more disposable containers 11, 12 and 13 of sterile wash solution, typically saline, one or more of which contain one or more treating reagents. For example, container 13 may typically contain suspended epithelial cells for coating the prosthesis. In general, reference will be made to "wash solutions" with the understanding that the solutions may be reagent solutions as well. The containers are designed to be suspended from a typical hospital hanger. Valves 14, 15 and 16 control the flow from the respective containers, permitting the use of one or more containers seriatim until a complete wash is accomplished. A master flow rate control valve 17 permits the operator to adjust the rate of flow through the chamber. A sterile filter 18 is desirably provided to provide additional assurance that the fluid entering the wash chamber 19 is perfectly sterile. If sterility is assured, and if particular types of reagents are to be included in some or all of the wash solution, the filter may be bypassed or omitted. For example, a valve 17a may open a bypass conduit to the wash chamber. A porcine heart valve 20 is mounted in the wash chamber on suitable supports to assure that it is in the proper configuration for use and to assure that the fluid flow will be uniform over the surface of the prosthesis being washed.

While the invention is illustrated as washing a porcine heart valve, the invention is equally applicable to washing and/or coating or treating other prosthetic devices, e. g. veins, arteries, and other tissue taken from pigs, other animals, or humans, all of which are known to be useful for implantation in humans. Human umbilical cords, for example, have been used as arterial grafts after fixation in glutaraldehyde. Similarly porcine and bovine arteries, and veins, have also been suggested for use as arterial grafts.

The effluent from the wash chamber passes, in a preferred embodiment, through a filter 21 and a ballcheck or other non-return check valve 22 to assure that no liquid can be forced or sucked back into the heart valve chamber. Valves 23a and 23b on the inlet and outlet of a reaction chamber 24 control flow through and permit isolation of the reaction chamber 24. An indicator containing solution is provided in the indicator container 25 and metered through a valve 26 into the reaction chamber 24. There are a number of indicators which may be used to permit detection of the presence or amount of various reagents. For example, where removal of glutaraldehyde is important, as is generally the case, several indicators react with aldehyde to provide a color reaction which is proportional to the amount of aldehyde present. Aldehydes will react, for example, with 2,4-dinitrophenylhydrazine to form an insoluble yellow or red solid. Aldehydes give a positive reaction with Tollens' reagent. Tollens' reagent contains the silver ammonia ion. Oxidation of the aldehyde is accompanied by reduction of the silver ion to free silver in the form of a mirror under proper conditions. Aldehydes are oxidized by oxidizing agents such as chromic anhydride and aqueous sulfuric acid. The clear orange solution formed by the combination of chromic anhydride and aqueous sulfuric acid turns blue-green and becomes opaque with the addition of aldehyde. A highly sensitive test for aldehydes is the Schiff test, in which an aldehyde reacts with the fuchsin-aldehyde reagent to form a characteristic magenta color. Typically a negative reaction with the above indicators is shown by no color change. The chamber 24 preferably ihcludes transparent walls to permit visual detection of colored species or silver in the above examples. Instrumental detection of, for example, redox potential may also be used.

While the previous example depicts an indicator chamber and reaction chamber as well as a indicator solution to determine the presence of preservatives, other effective devices such as a polarimeter, oxidation-reduction cell, membrane electrode, or other means can be used to determine the presence of preservatives on or within the heart valve prosthesis.

Figure 2:
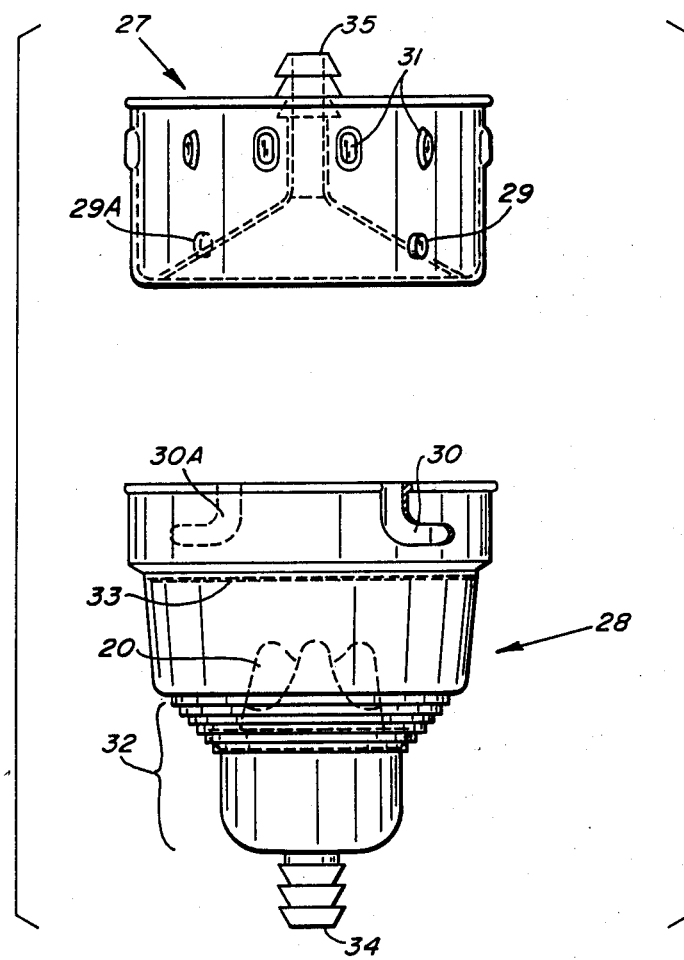
FIG. 2 is an exploded side view of the wash chamber of this invention.

As shown in greater detail in FIG. 2 the wash chamber is in the form of a heart valve support and container comprising a removable cap 27, connected to a funnel 28. The cap is provided with protuberances 29 and 29A which are recieved and rotated in the slots 30 and 30A to form a bayonet lock. A threaded or other type of connection can be used also, but the bayonet type interlocking mechanism is convenient, secure and easily connected and opened. The cap has finger grips 31 to facilitate the locking and unlocking of the cap with the funnel. The heart valve prosthesis 20 is placed in the large end of the funnel 32 on supports to assure the proper configuration of the valve and permit reasonably uniform flow of fluid over the valve. The particular support will be configured, dimensioned and constructed according to the configuration of the particular prosthesis being shipped, stored and washed. A filter cloth 33 optionally surrounds the prosthesis 20, breaking down any fast jets of wash solution and assuring a diffuse flow of solution over all surfaces of the prosthesis. The cap, which is the inlet portion to the wash chamber, is designed to cause the wash solution to flow in a relatively high velocity flow, with low volume over all surfaces of the prosthesis, thus providing a continuing source of fresh wash solution to assure that the concentration differential between the solution on and in the tissue and the wash solution is maximum and thus maximize the migration of preservative from the tissue to the wash solution. A high velocity, relatively thin layer and low volume of the wash solution is formed by the inner walls of the funnel around the valve. Tube connectors 34, on the funnel, and 35 on the cap are configured, constructed and adapted to be connected to tubes from the containers saline wash solution.

Figure 3:
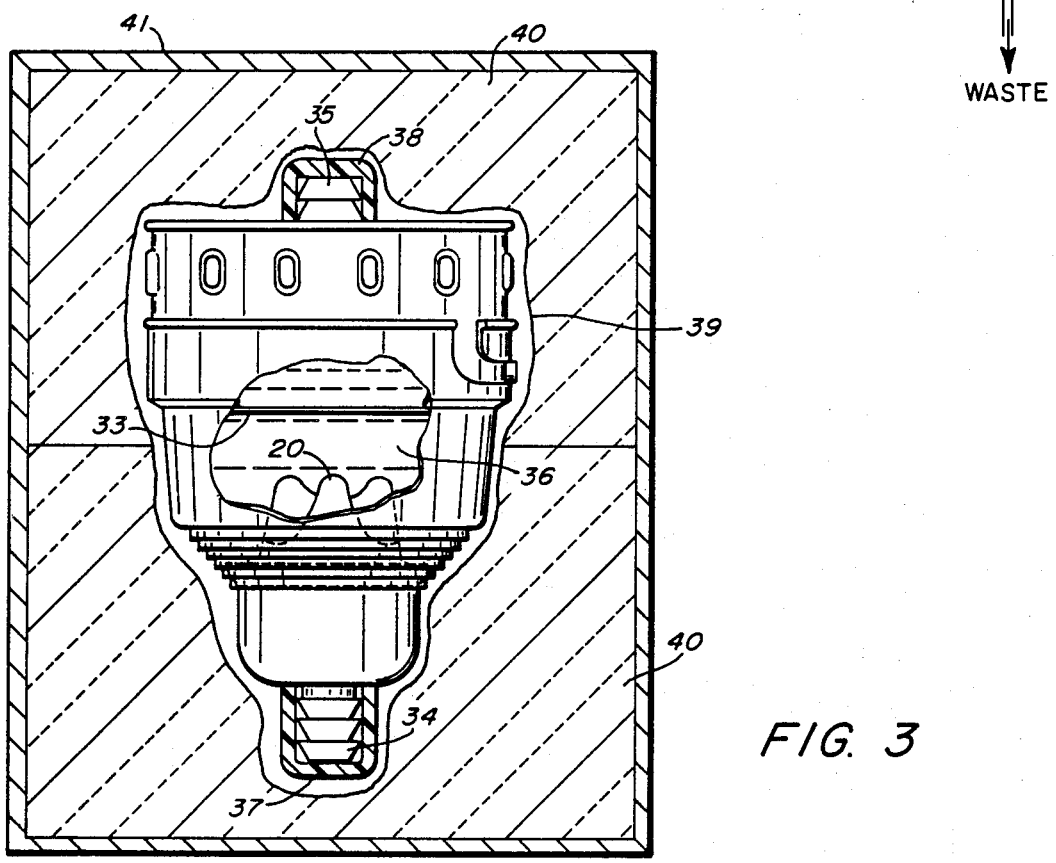
FIG. 3 is a partially cut away side view of the packaged wash chamber of this invention.

FIG. 3 depicts the wash chamber, which also serves to contain the prosthesis and protect it during shippment and storage, as part of an integral package protected against extremes of temperature and shock. The heart valve prosthesis 20 is placed wash chamber and covered by storage preservative solution, indicated at 36. Cap seals 37 and 38 are placed on the connecting devices 34 and 35 to maintain the storage solution in the heart valve rinser. The rinser is placed in a heat sealable polyethylene pouch 39. The pouch is sealed to serve as a tamper indicator and dust/lint protector and to maintain sterility. The pouch and rinser are placed in a expanded polystyrene shell 40 which prevents rapid and extreme changes in temperature during temporary shipment and as a protection against shock and physical damage. The expanded polystyrene shell is then placed in a corrugated carton 41 for shipment and storage.

Figure 4:
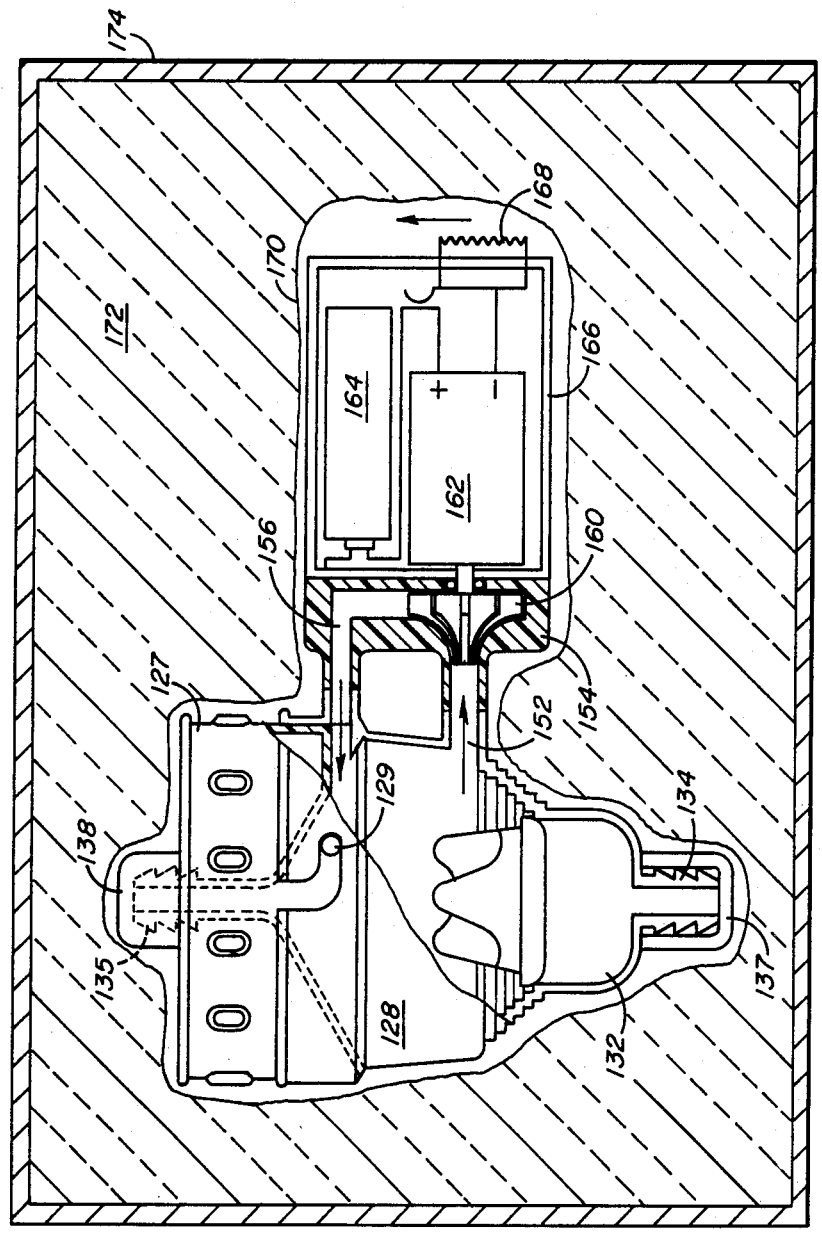
FIG. 4 is a sid view, partially cut away and in partial cross-section showing the wash chamber of the invention unitarily associated with a recirculating pump.

Reference is now made to FIG. 4 in connection with FIGS. 2 and 3. A preferred embodiment of this invention which includes a built-in recirculation system is depicted in FIG. 4. The wash chamber in FIG. 4 is identical to that shown in FIGS. 2 and 3 with the addition of inlet and outlet conduits for recirculation. Cap 127 and funnel 128 interlock using a boss 129 in a bayonet connector, have fluid conduit connectors 134 and 135 and caps 137 and 138 all as described above respecting the corresponding elements 27, 28, 29, 34, 35, 37, and 38, except as described below. The funnel 128 is provided with a conduit 152 which provides fluid communication into a pump chamber 154 and back through a conduit 156, a portion of which 156a is formed as part of the cap 127, into the wash chamber. Alternatively, the conduit 156 may bypass the cap 127 and connect directly back into the funnel 128. An impeller 160 is mounted in the pump chamber 154 and is connected to a motor 162 driven by a battery 164, or a plurality of batteries, the entire pump drive assembly being packaged in a housing 166. A slide switch 168 is mounted in the housing for turning the motor on and off. Any reliable switch may be used. As is the case in the previous embodiments, the wash chamber, including in this case the built in recirculation pump, is enclosed in an airtight envelope 170 which, in turn, is packaged against shock and physical damage by packing 172 and a case 174 which may be of the type previously described or of any other suitable type.

The system of this invention is most conveniently shipped together with all components and reagents in two, or more, packages marked to identify a complete system. The wash chamber and prosthesis contained therein is typically shipped in a separate container, because of the need to have various sizes and types of prosthesis on hand. Thus, for example, a complete system would include in one container of the type shown in FIGS. 3 or 4 the implant prosthesis in a wash chamber and in another container one or more, typically three, containers of wash solution, the valves, tubing, chambers, filters and reagents necessary to complete a system as schematically depicted in FIG. 1. All of the components are typically pre-sterilized and sealed in tamper proof or tamper indicator packages, or in packages which permit sterilization by the hospital.

In or adjacent the operating room, the system is assembled as indicated in FIG. 1, the solution from the first container is caused to flow by gravity or pumping over the prosthesis. Periodic checks, at different periods depending upon the prosthesis and nature and concentration of the preservative solution, are made using the indicator means described to monitor the preservative content of the effluent of the wash chamber. As needed, the wash solution from the various containers is caused to flow over the prosthesis until the effluent tests absolutely free of the preservative, or the level is low enough to assure that no adverse physiological reaction will occur. In some instances, the configuration of a prosthesis may be constant enough to provide an impirical basis for determining that a complete wash is accomplished when a predetermined volume of wash solution has been caused to flow over the prosthesis.

Higher washing and/or treating efficiency is provided using the recirculation pump, especially during washing. One of the containers, e. g. container 13 may contain epilethial cells or other treating cells and/or reagents, which will be cause to flow over the prosthesis after washing is complete or essentially complete for pre-treating the prosthesis by coating, reaction or otherwise.

Industrial Application

This invention finds application in the surgical arts.
What is claimed is:

1. A packaged prosthesis comprising, in combination, a wash chamber comprising top and bottom portions removeably secured together in fluid tight sealed contact, a prosthesis in the wash chamber, the wash chamber comprising means for supporting the prosthesis and, in use, for directing flow of fluid over all surfaces thereof, fluid inlet means on the top, fluid outlet means on the bottom, removeable seals on the respective fluid inlet and outlet means, sterile preservative fluid in the chamber for maintaining the sterility and physical or chemical condition, or both, of the prosthesis contained therein, a protective wrapper entirely enclosing the wash chamber, and means for protecting the chamber from shock and damage enclosing the chamber, the wash chamber being so constructed and configured as to be connectable with a source of sterile wash solution to thereby cause the wash solution flow over the prosthesis for removing chemicals therefrom or treating the prosthesis, or both, all without breaching the sterility of the wash chamber.

2. The packaged prosthesis of claim 1, wherein:
said wash chamber comprises a funnel and a cap forming said wash chamber said wash chamber being constructed, configured and dimensioned to receive a heart valve prosthesis and, in use, to direct fluid flow over all surfaces thereof, said cap being removeably connected to said funnel, and in fluid communication with said sterile filter,; and a filter cloth in said funnel for covering said heart valve prosthesis positioned within said funnel for spreading fluid flow and causing flow over all surfaces of the prosthesis.

3. The packaged prosthesis of claim 2 further comprising:

a recirculation outlet conduit in fluid communication with the wash chamber, a recirculation inlet conduit in fluid communication with the wash chamber, and means for recirculating fluid through the wash chamber and said recirculation conduits to provide additional washing of the prosthesis.

4. The packaged prosthesis of claim 1 further comprising:

a recirculation outlet conduit in fluid communication with the wash chamber, a recirculation inlet conduit in fluid communication with the wash chamber, and means for recirculating fluid through the wash chamber and said recirculation conduits to provide additional washing of the prosthesis.

* * * * *